US005888965A

United States Patent [19]
Kmiecik et al.

[11] Patent Number: 5,888,965
[45] Date of Patent: Mar. 30, 1999

[54] METHOD OF STIMULATING BONE MARROW REGENERATION

[75] Inventors: Thomas E. Kmiecik, Frederick, Md.; George F. Vande Woude, Berryville, Va.

[73] Assignee: The United States of America as represented by the Department of Health and Human Services, Washington, D.C.

[21] Appl. No.: 242,343

[22] Filed: May 13, 1994

Related U.S. Application Data

[60] Division of Ser. No. 914,630, Jul. 20, 1992, Pat. No. 5,362,716, which is a continuation-in-part of Ser. No. 830,586, Feb. 6, 1992, abandoned, which is a continuation-in-part of Ser. No. 642,971, Jan. 18, 1991, Pat. No. 5,648,273, which is a continuation-in-part of Ser. No. 457,556, Dec. 27, 1989, abandoned, and Ser. No. 582,063, Sep. 14, 1990, abandoned.

[51] Int. Cl.$^6$ .......................... A61K 38/17; A61K 38/20
[52] U.S. Cl. .............................. 514/2; 530/351; 530/399; 435/183; 424/85.2; 424/85.1
[58] Field of Search ................................. 424/85.2, 85.1; 514/2, 12; 530/351, 399; 435/183

[56] References Cited

U.S. PATENT DOCUMENTS

| 5,004,805 | 4/1991 | Gohda et al. | 530/399 |
|---|---|---|---|
| 5,227,158 | 7/1993 | Jardieu . | |

FOREIGN PATENT DOCUMENTS

| 350641 | 1/1990 | European Pat. Off. . |
|---|---|---|
| 0 461560 | 12/1991 | European Pat. Off. . |
| 462277 | 12/1991 | European Pat. Off. . |
| 462549 | 12/1991 | European Pat. Off. . |

OTHER PUBLICATIONS

Hunter et al., "Preparation of Iodine–131 Labelled Human Growth Hormone of High Specific Acivity," *Nature*, vol. 194, No. 4827, pp. 495–496 (May 1962).

Laemmli, "Cleavage of Structural Proteins During the Assembly of the Head of Bacteriophage T4," *Nature*, vol. 227, pp. 680–685 (Aug. 1970).

Stanley et al., "Standardized Bioassay for Bone Marrow Colony Stimulating Factor in Human Urine: Levels in Normal Man," *J. Lab Clin. Med.* vol. 79, pp. 657–668 (Apr. 1972).

Köhler et al., "Continuous Cultures of Fused Cells Secreting Antibody of Predefined Specificity," *Nature*, vol. 256, pp. 495–497 (1975).

Holmes et al., "Correlation of Cell–Surface Phenotype with the Establishment of Interleukin 3–Dependent Cell Lines From Wild–Mouse Murine Leukemia Virus–Induced Neoplasms," *Proc. Natl. Acad. Sci. USA*, vol. 82, pp. 6687–6691 (Oct. 1985).

Stoker et al., "Scatter Factor is a Fibroblast–Derived Modulator of Epithelial Cell Mobility," *Nature*, vol. 327, pp. 239–242 (May 1987).

Park et al., "Sequence of MET Protooncogene cDNA has Features Characteristic of the Tyrosine Kinase Family of Growth–Factor Receptors," *Proc. Natl. Acad. Sci. USA*, vol. 84, pp. 6379–6383 (Sep. 1987).

Ikebuchi et al., "Interleukin 6 Enhancement of Interleukin 3–Dependent Proliferation of Multipotential Hemopoietic Progenitors," *Proc. Natl. Acad. Sci. USA*, vol. 84, pp. 9035–9039 (Dec. 1987).

Gonzatti–Haces et al., "Characterization of the TPR–MET Oncogene p65 and the MET Protooncogene p140 Protein–Tyrosine Kinases," *Proc. Natl. Acad. Sci. USA*, vol. 85, pp. 21–25 (Jan. 1988).

Gohda et al., "Purification and Partial Characterization of Hepatocyte Growth Factor from Plasma of a Patient with Fulminant Hepatic Failure," *J. Clin. Invest.*, vol. 81, pp. 414–419 (Feb. 1988).

Shoelson et al., "Tryptic Activation of the Insulin Receptor," *The Journal of Biological Chemistry*, vol. 263, No. 10, pp. 4852–4860 (Apr. 1988).

Leary et al., "Synergism Between Interleukin–6 and Interleukin–3 in Supporting Proliferation of Human Hematopoietic Stem Cells: Comparison With Interleukin–1α," *Blood*, vol. 71, No. 6, pp. 1759–1763 (Jun. 1988).

Chan et al., "Characterization of the Mouse MET Proto–Oncogene," *Oncogene*, vol. 2, pp. 593–599 (1988).

Tempest et al., "Structure of the MET Protein and Variation of MET Protein Kinase Activity Among Human Tumour Cell Lines," *Br. J. Cancer*, vol. 58, pp. 3–7 (1988).

Hara et al., "Bipotential Murine Hemopoietic Cell Line (NFS–60) That is Responsive to IL–3, GM–CSF, G–CSF, and Erythropoletin," *Exp. Hematol.*, vol. 16, pp. 256–261 (1988).

Stern et al., "EGF–Stimulated Tyrosine Phosphorylation of p185$^{neu}$: A Potential Model for Receptor Interactions," *EMBO Journal*, vol. 7, No. 4, pp. 995–1001 (1988).

King et al., "EGF Binding to its Receptor Triggers a Rapid Tyrosine Phosphorylation of the erbB–2 Protein in the Mammary Tumor Cell Line SK–BR–3," *EMBO Journal*, vol. 7, No. 6, pp. 1647–1651 (1988).

Zarnegar et al., "Purification and Biological Characterization of Human Hepatopoietin A, a Polypeptide Growth Factor for Hepatocytes," *Cancer Research*, vol. 49, pp. 3314–3320 (Jun. 1989).

(List continued on next page.)

*Primary Examiner*—Sally P. Teng
*Attorney, Agent, or Firm*—Needle & Rosenberg, P.C.

[57] ABSTRACT

The present invention relates to a complex comprising hepatocyte growth factor (HGF) and met proto-oncogene protein. The present invention also relates to methods for detecting the presence of HGF ligand, met proto-oncogene receptor and methods for isolating either the ligand or receptor or complex comprising both. The present invention further relates to methods of diagnostic proliferative disorders and diseases such as hepatitis or hepatocarcinogenesis by detecting these ligand-receptor pairs.

6 Claims, 6 Drawing Sheets

OTHER PUBLICATIONS

Gherardi et al., "Purification of Scatter Factor, A Fibroblast–Derived Basic Protein that Modulates Epithelial Interactions and Movement," *Proc. Natl. Acad. Sci. USA*, vol. 86, pp. 5844–5848 (Aug. 1989).

Miyazawa et al., "Molecular Cloning and Sequence Analysis of cDNA for Human Hepatocyte Growth Factor," *Biochemical and Biophysical Research Communications*, vol. 163, No. 2, pp. 967–973 (Sep. 1989).

Nakamura et al., "Molecular Cloning and Expression of Human Hepatocyte Growth Factor," *Nature*, vol. 342, pp. 440–443 (Nov. 1989).

Kinoshita et al., "Marked Increase of HGF mRNA in Non–Parenchymal Liver Cells of Rats Treated with Hepatotoxins," *Biochem. and Biophys. Res. Communications*, vol. 165, No. 3, pp. 1229–1234 (Dec. 1989).

Giordano et al., "Biosynthesis of the Protein Encoded by the C–MET Proto–Oncogene," *Oncogene*, vol. 4, pp. 1383–1388 (1989).

Iyer et al., "Structure, Tissue–Specific Expression, and Transforming Activity of the Mouse met Protooncogene," *Cell Growth & Differentiation*, vol. 1, pp. 87–95 (1990).

Keller et al., "Transforming Growth Factor β Directly Regulates Primitive Murine Hematopoietic Cell Proliferation," *Blood*, vol. 75, No. 3, pp. 596–602 (Feb. 1990).

Zarnegar et al., "Tissue Distribution of Hepatopoietin–A: A Heparin–Binding Polypeptide Growth Factor for Hepatocytes," *Proc. Natl. Acad. Sci. USA*, vol. 87, pp. 1252–1256 (Feb. 1990).

Tashiro et al., "Deduced Primary Structure of Rat Hepatocyte Growth Factor and Expression of the mRNA in Rat Tissues," *Proc. Natl. Acad. Sci. USA*, vol. 87, pp. 3200–3204 (Apr. 1990).

Bottaro et al., "Characterization of the Receptor for Keratinocyte Growth Factor," *The Journal of Biological Chemistry*, vol. 265, No. 22, pp. 12767–12770 (Aug. 1990).

Weidner et al., "Scatter Factor: Molecular Characteristics and Effect on the Invasiveness of Epithelial Cells," *The Journal of Cell Biology*, vol. 111, pp. 2097–2108 (Nov. 1990).

Kuma et al., "Effect of Human Recombinant Interleukin–6 on the Proliferation of Mouse Hepatocytes in the Primary Culture," *Immunobiol.*, vol. 180, pp. 235–242 (1990).

Roidan et al., "Cloning and Expression of the Receptor for Human Urokinase Plasminogen Activator, a Central Molecule in Cell Surface, Plasmin Dependent Proteolysis," *EMBO Journal*, vol. 9, pp. 467–474 (1990).

Rubin et al., "A Broad–Spectrum Human Lung Fibroblast–Derived Mitogen is a Variant of Hepatocyte Growth Factor," *Proc. Natl. Acad. Sci. USA*, vol. 88, pp. 415–419 (Jan. 1991).

Gherardi et al., "Hepatocyte Growth Factor—Scatter Factor: Mitogen, Motogen, and Met," *Cancer Cells*, vol. 3, No. 6, pp. 227–232 (Jun. 1991).

Rodrigues et al., "Alternative Splicing Generates Isoforms of the met Receptor Tyrosine Kinase Which Undergo Differential Processing," *Molecular and Cellular Biology*, vol. 11, No. 6, pp. 2962–2970 (Jun. 1991).

Weidner et al., "Evidence for the Identity of Human Scatter Factor and Human Hepatocyte Growth Factor," *Proc. Natl. Acad. Sci. USA*, vol. 88, pp. 7001–7005 (Aug. 1991).

Y. Daikuhara et al., "Monoclonal Antibody", *Patent Abstracts of Japan: Unexamined Applications*, 13(174): p. 19 C 589, Abstract 64–3 199 (Apr. 25, 1989).

Y. Daikuhara, et al., "Monoclonal Antibody", *Patent Abstracts of Japan: Unexamined Applications*, 13(208): p. 120 C 596, Abstract 1–27491 (May 16, 1989).

METHOD OF STIMULATING BONE MARROW REGENERATION

This application is a division of application Ser. No. 07/914,630, filed Jul. 20, 1992, which issued as U.S. Pat. No. 5,362,716 on Nov. 8, 1994, and which is a continuation-in-part of application Ser. No. 07/830,586 filed Feb. 6, 1992, now abandoned, which is a continuation-in-part of application Ser. No. 07/642,971 filed Jan. 18, 1991, U.S. Pat. No. 5,648,273, which is a continuation-in-part of application Ser. No. 07/457,556 filed Dec. 27, 1989, now abandoned and Ser. No. 07/582,063 filed Sep. 14, 1990 now abandoned.

BACKGROUND OF THE INVENTION

1. Technical Field

The present invention relates to a complex comprising hepatocyte growth factor (HGF) and the met proto-oncogene protein. The present invention also relates to a method for detecting the presence of HGF ligand or met proto-oncogene receptor and to a method for isolating either the ligand, the receptor or a complex comprising both.

The present invention further relates to methods of diagnosing and treating conditions proliferative disorders such as hepatitis, hepatocarcinogenesis, carcinogenesis and wound healing.

Further, the present invention relates to a method of stimulating the proliferation of hemtopoietic progenitors with HGF.

2. Background of the Invention

Hepatocyte growth factor (HGF) was first purified from human and rabbit plasma and rat platelets on the basis of its ability to stimulate mitogenesis of rat hepatocytes (Gohoda et al. *J Clin. Invest.* 81, 414 (1988); Zarnegar et al. *Cancer Res.* 49, 3314 (1989); Nakamura et al. *FEBS Lett.* 224, 311 (1987)). Thus, HGF may act as a humoral factor promoting liver regeneration after partial hepatectomy or liver injury (Michalopoulos *FASEB J.* 4, 176 (1990)). The same factor was purified from human fibroblast culture medium and shown to act on melanocytes and a variety of epithelial and endothelial cells (Rubin et al. *Proc. Natl. Acad. Sci. USA* 88, 415 (1990)). Together with evidence of HGF expression in several organs (Rubin et al. *Proc. Natl. Acad. Sci. USA* 88, 415 (1990); Tashiro et al. *Proc. Natl. Acad. Sci. USA* 87, 3200 (1990); Zarnegar et al. *Proc. Natl. Acad. Sci. USA* 87, 1252 (1990); Kinoshita et al. *Biochem. Biophys. Res. Comm.* 165, 1229 (1989)), these findings indicate that HGF may also act as a paracrine mediator of proliferation for a broad spectrum of cell types. Molecular cloning of HGF revealed a remarkable structural homology to plasminogen and related serine proteases (Rubin et al. *Proc. Natl. Acad. Sci. USA* 88, 415 (1990); Nakamura et al. *Nature* 342, 440 (1989); Miyazawa et al. *Biophys. Res. Comm.* 163, 967 (1989)). Recent evidence that HGF induces rapid tyrosine phosphorylation of proteins in intact target cells suggests that a tyrosine kinase receptor might mediate its mitogenic signal (Rubin et al. *Proc. Natl. Acad. Sci. USA* 88, 415 (1990)).

HGF is structurally related to the family of serine proteases that includes plasminogen, prothrombin, urokinase, and tissue plasminogen activator (Rubin et al. *Proc. Natl. Acad. Sci. USA* 88, 415 (1990)); Nakamura et al. *Nature* 342, 440 (1989)). As defined herein, HGF includes a variant of HGF previously characterized as a broad-spectrum mitogen called plasminogen like growth factor (PLGF). Several proteases, including members of the serine protease family, stimulate DNA synthesis presumably through a proteolytic mechanism similar to tryptic activation of the insulin receptor (Shoelson et al. *J. Biol. Chem.* 263, 4852 (1988)). To date, only urokinase has been found to associate with a specific cell-surface receptor, which itself bears no homology to any known tyrosine kinase receptors (Roldan et al. *EMBO J.* 9, 467 (1990)). It has recently been observed that HGF is very similar or identical to scatter factor (Gherardi, et al. *Nature* 346, 28 (1990) Gherardi, et al. *Cancer Cells* 3, 227–232 (1991); Weidner, et al. *Proc. Nat. Acad. Sci. USA* 88, 7001–7005 (1991)). Scatter factor has been characterized as causing epithelial cells to dissociate from each other and begin migration (Gherardi, et al. *Proc. Nat. Acad. Sci. USA* 86, 5844–5848 (1989); Weidner, et al. *J. Cell Biol.* 111, 2097–2108 (1990); Stoker, et al. *Nature* 327, 239–242 (1987)). These observations suggest that HGF might function in the growth-and renewal of epithelial cells that would be required in wound repair. Further, under proper conditions, HGF may have a stimulatory, as well as inhibitory, effect on hematopoietic cells.

It is clear that a need exists to identify the receptor of HGF. The present invention provides such a receptor, which receptor is the met proto-oncogene product, and a complex comprising HGF and met proto-oncogene protein. The met proto-oncogene protein is a member of the tyrosine kinase growth factor receptor family.

cMet mRNA has been detected in several murine myeloid progenitor tumor cell lines (Iyer et al. *Cell Growth and Diff.* 1, 87–95 (1990)), raising the question whether HGF might be mitogenic for these cell lines. The effect of HGF on the growth and inhibition of one such cell line, NFS-60, has been examined. The NFS-60 cell line requires IL-3 to maintain its growth in vitro and is representative of an immature hematopoietic progenitor blocked in differentiation (Holmes et al. *Proc. Nat. Acad. Sci. USA* 82, 6687–6691 (1985); Hara et al. *Exp. Hematol.* 16, 256–261 (1988)). It has previously been shown to express significant levels of met mRNA (Iyer et al. *Cell Growth and Diff.* 1, 87–95 (1990)). The ability of HGF to stimulate [$^3$H] thymidine incorporation into NFS-60 cells was examined.

These findings, combined with the previously documented effects of HGF upon hepatocytes, epithelial cells, endothelial cells, and melanocytes, taken with the apparent close relationship between scatter factor and human growth factor, demonstrate that HGF is a growth factor for renewable cells from a variety of tissues. The ability of HGF to stimulate both liver regeneration and myeloid progenitors is strikingly similar to the effects of IL-6, which has been shown to induce proliferation of hepatocytes (Kuma, et al. *Immunobiol.* 180, 235–242 (1990)), and to act as a synergistic factor for IL-3 dependent colony formation (Ikebuchi, et al. *Proc. Natl. Acad. Sci. USA* 84, 9035–9039 (1987); Leary, et al. *Blood* 71, 1759–1763 (1988)).

Knowledge of the receptor/ligand relationship involving HGF will facilitate the study and treatment of proliferative disorders in which expression of these molecules plays an important role. Additionally, identification of the met proto-oncogene receptor-HGF complex provides a means for identifying tissues other than liver tissue affected by factor binding.

SUMMARY OF THE INVENTION

It is an object of the present invention to provide a complex comprising a hepatocyte growth factor (HGF) ligand and met proto-oncogene protein receptor and methods of utilizing the complex.

It is another object of the present invention to provide a method of stimulating the proliferation of hematopoietic progenitors.

It is yet another object of the present invention to provide a method of inhibiting the proliferation of hematopoietic progenitors.

It is a further object of the present invention to provide antibodies which recognize and react with any of the group consisting of HGF, met proto-oncogene receptor protein, and HGF-met proto-oncogene receptor protein complex.

Various other objects and advantages of the present invention will become apparent from the Figures and the following description of the invention.

The present invention relates to a method for detecting HGF (ligand) or met/proto-oncogene product (receptor) and to a method for isolating either the ligand, the receptor or a complex comprising both. The present invention also relates to methods of diagnosing and treating proliferative disorders. The present invention further relates to a method of stimulating and inhibiting, under proper conditions, the proliferation of hematopoietic progenitors with HGF.

BRIEF DESCRIPTION OF THE DRAWINGS

FIG. 1. Tyrosine phosphorylation of p145 in B5/589 human mammary epithelial cells in response to HGF.

FIG. 2. Identification of p145 as the B-subunit of the c-met proto-oncogene product.

FIG. 3 Covalent affinity cross-linking of $^{125}$labeled HGFp28 to the c-met protein-tyrosine kinase.

FIG. 4. [$^3$H]thymidine uptake of NFS-60 cells.

(FIG. 6A) HGF was added in combination with GM-CSF. (FIG. 6B) HGF was added in combination with IL-3. A modification of the method of Stanley et al. (*J. Lab. Clin. Med.* 79:657–668 (1972)) was used to measure colony formation of lin-cells. Lin- bone marrow cells were suspended in 1 ml RPMI 1640, 10% FCS, and 0.3% Seaplaque agarose (Rockland, Me.), and incubated in 35-mm Lux Petri dishes (Miles Scientific, Naperville, Ill.) at 37° C. in 5% $CO_2$ and scored for colony growth.

DETAILED DESCRIPTION OF THE INVENTION

Figure 1A:
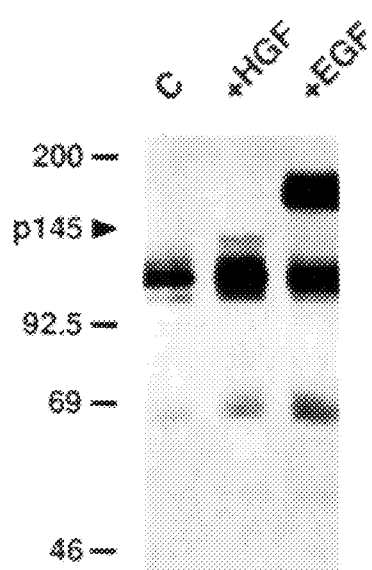
FIG. 1A. Immunoblot of phosphotyrosyl proteins from untreated control cells (lane 1), cells treated with HGF, and with EGF (Collaborative Research). HGF was purified as described elsewhere (Rubin et al. Proc. Natl. Acad. Sci, USA 88, 415 (1990)). Serum-starved cells were exposed to growth factor (100 ng/ml) for 10 min at 37° C. as indicated, detergent-solubilized on ice, and immunoprecipitated with monoclonal anti-pTyr (Upstate Biotechnology). Immunoprecipitated proteins were resolved by 7.5% SDS polyacrylamide gel electrophoresis (SDS-PAGE) (Laemmli Nature 227, 680 (1970)), and immunoblotted with the same antibody as described elsewhere (Bottaro et al. J. Biol. Chem. 265, 12767 (1990)).

The present invention relates generally to a complex comprising HGF and its receptor, met proto-oncogene protein. The binding of HGF to its receptor regulates the intrinsic tyrosine kinase activity of the receptor. Accordingly, the present invention further relates to methods of utilizing the complex.

One embodiment of the present invention relates to a complex formed by the interaction of HGF with the met proto-oncogene protein. In a preferred embodiment, the complex is free of protein with which it is naturally associated.

The direct interaction of HGF with the c-met receptor tyrosine kinase suggests a biochemical mechanism of mitogenic signal transduction similar to that of insulin, EGF and other peptide growth factors. This interaction represents a significant functional divergence from HGF's structurally related family of serine protease homologs. HGF is homologous to the serine protease family, but does not contain the necessary amino acids that would allow it to function as a protease. Since it cannot function as a protease, but binds to a tyrosine kinase, its method of signal transduction must differ from other members of the serine protease family.

The present invention also relates to detection and quantitation methods that can be used in diagnostics to identify HGF (ligand), met proto-oncogene product (receptor) or the ligand-receptor complex. Since the met-proto-oncogene receptor is expressed in many cell types and tissues, including the liver, the methods described herein provide a means for identifying tissues other than liver affected by HGF binding. The methods of the present invention also aid in understanding the role of the interaction between receptor and ligand in regulating biochemical and physiological mechanisms in a broad spectrum of tissues.

Antibodies can be raised to the HGF-receptor complex, or unique portions thereof, both in its naturally occurring form and in its recombinant form. The invention relates to antibodies specific for that complex.

The HGF-receptor complex or reactive fragments thereof can be joined to other materials, particularly polypeptides, as fused or covalently joined polypeptides to be used as immunogens. The HGF-receptor complex and its functional fragments can be fused or covalently linked to a variety of immunogens, such as keyhole limpet hemocyanin, bovine serum albumin, tetanus toxoid, etc. See for example, *Microbiology* Hoeber Medical Division (Harper and Row, 1969), Landsteiner, *Specificity of Serological Reactions* (Dover Publications, New York, 1962) and Williams et al. *Methods in Immunology and Immunochemistry*, Vol. 1 (Academic Press, New York, 1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., editors, *Basic and Clinical Immunology*, (Lange Medical Publications, Los Altos, Calif., Fourth edition) and references cited therein, and in particular in Kohler and Milstein in *Nature* 256:495–497 (1975), which discusses one method of generating monoclonal antibodies.

The present invention further relates to a method of detecting and quantitating HGF receptor in a biological sample using labeled HGF as a probe. Suitable labels include, for example, radiolabels such as $^{125}I$, and fluorescene.

Using standard methodologies well known in the art, a biological sample can be extracted with a non-ionic detergent and incubated with labeled HGF in the presence or absence of unlabeled HGF. The resulting complex can be separated from the uncomplexed (or unbound) labeled material, for example, by immunoprecipitating the complex with a specific polyclonal or monoclonal antibody that recognizes the met proto-oncogene receptor protein or the HGF-met proto oncogene receptor complex. The overall signal resulting from the presence of label associated with the resulting complex is compared with the signal from a background, blank sample as is well known in the art. Alternatively, the complex may be separated from uncomplexed material by precipitating with polyethylene glycol. In both methodologies, the amount of label that is immunoprecipitated or precipitated is directly related to the amount of complex in the biological sample.

The present invention also relates to a method for detecting and quantitating HGF in a biological sample using labeled HGF receptor as a probe. The method is carried out as a reciprocal binding assay following the methodology described above except substituting as antibody, one that specifically recognizes HGF or the HGF-met proto-oncogene receptor complex.

The present invention further relates to methods of detecting and quantitating the HGF-met proto-oncogene receptor complex in a sample. In one preferred embodiment, the complex is detected and quantitated using antibodies. Antibodies utilized in this embodiment can be directed against HGF, met-proto-oncogene receptor protein or the HGF-receptor complex. Antibodies can be either polyclonal or monoclonal. A sample can be extracted with non-ionic detergent and incubated with labeled HGF or met proto-oncogene receptor protein. After incubation, the sample can be covalently cross-linked with a bifunctional reagent such as a chemical cross-linker, for example, disuccinimidyl suberate (DSS). After quenching the reaction with a quenching agent, the sample can be immunoprecipitated with specific antibody or precipitated with polyethylene glycol. Quantitation requires chromatographic separation by, for example, gel electrophoresis, followed by autoradiography.

In another embodiment, the invention relates to a method for detecting HGF-met proto-oncogene receptor complexes in a sample, the simultaneous expression of HGF and met proto-oncogene receptor mRNAs are determined.

Simultaneous co-expression of HGF and met proto-oncogene receptor can be determined by Northern analysis using oligo- or cDNA probes derived from the sequence of either gene to identify mRNA or using the polymerase chain reaction (PCR) or any combination known to one skilled in the art. Northern analysis and the PCR technology are methods well known to those skilled in the art.

The present invention further relates to diagnostic methodologies using the methods described above. The disorders detected by the methods of the present invention can include, for example, proliferative disorders such as hepatocellular carcinoma or other carcinomas of tissues that normally express met proto-oncogene receptor. Such tissues can be derived from epithelial cells such as skin, lung, stomach, kidney or colon, liver or endothelial cells, such as those contained in the vascular lining or bone marrow, or hematopoietic stem cells. The present diagnostic methods can also be used to measure wound repair in tissues derived from the cells described above, and in cells that normally express HGF such as platelets, fibroblasts (stromal tissue of skin and other organs) and spleen.

Inactivation of the HGF-met mitogenic pathway provides the basis for therapeutic methodologies designed to diminish or arrest normal or pathological cell proliferation. These methodologies include the production of chemically or genetically engineered HGF derived species that lack or possess an impaired met-binding domain, or that lack or possess an impaired activating domain, but that otherwise retain the structural and biochemical characteristics of HGF. Such techniques of chemical or genetic engineering are well known to one skilled in the art. Similarly, production of genetically engineered met species that lack or possess an impaired HGF-binding domain, or lack or possess an impaired tyrosine kinase domain, but which otherwise retain the structural and biochemical characteristics of the met protein are also included.

These methodologies further include the production of a water-soluble form of the met protein consisting of the extracellular HGF-binding domain that can act as an antagonist of normal met protein activation by HGF. The delivery of the chemically or genetically engineered HGF or met protein species described above to the selected site of action may be achieved using conventional methods of drug delivery, gene transfer, or any combination thereof known to one skilled in the art.

Artificial activation of the HGF-met mitogenic pathway provides the basis for therapeutic methodologies designed to restore, replace, or enhance naturally occurring wound repair mechanisms. These methodologies include application to the wound site of chemically or genetically engineered or derived HGF or met species that enhance the binding interaction between met protein and HGF and thereby create an artificially sustained HGF-met interaction. For example, site-directed mutagenesis of the HGF-binding domain of met, or the met-binding domain of HGF (or both), may be used to create a member of the HGF/met pair with higher binding affinity for the other member of the pair and thus affect accelerated growth or regeneration of the wounded tissue.

Similarly, conventional recombinant DNA techniques could be used to enhance or sustain the kinase activity of the met protein normally regulated by HGF binding, including met mutations possessing a constitutively activated tyrosine kinase. The delivery of the genetically engineered HGF or met protein species described above to the selected site of action can be achieved using conventional methods of drug delivery, gene transfer, or any combination thereof well known to one skilled in the art. Activation of the HGF-met mitogenic pathway by means of supplementing the natural expression of met by recombinant DNA techniques or chemical derivation, in combination with exogenously administered HGF is also included.

Further, several lymphokine-lymphokine receptor pairs have been seen to regulate hematopoiesis. The role of HGF and met proto-oncogene product in hematopoiesis discovered in the present invention provides facets of hematopoietic regulation previously unknown. HGF may be useful alone or in combination with other lymphokines in stimulating or inhibiting hematopoiesis.

Met expression has been demonstrated in myeloid leukemia lines and HGF has been found to be the ligand for met protein. The present invention demonstrates that HGF functions to regulate hematopoiesis. One skilled in the art will realize that this invention provides for methods of stimulating bone marrow regeneration, treating leukemia or stimulating the immune response to infection.

In one embodiment of this aspect of the invention, such a treatment method can include HGF, HGF-receptor complex, or met protein receptor alone or in combination with stress antigens. The chosen antigen can be delivered to a mammal in a pharmacologically acceptable vehicle. As one skilled in the art will understand, it is- not necessary to use the entire HGF, HGF-receptor or met protein receptor in entirety. An immunogenic portion of these proteins can be used. As will be realized by one skilled in the art, such a vaccine, or treatment of the invention can include an effective amount of an immunological adjuvant known to enhance an immune response. The proteins or polypeptides are present in the treatment formulation in an amount sufficient to induce immune response against the antigenic protein or proteins and thus to produce the desired stimulation or suppression of the hematopoietic or immune system. The antigen can be administered in a variety of manners including absorbing to aluminum hydroxide or phosphate; conjugated to a carbohydrate or carrier protein; administered with an adjuvant such as maramuyl peptide or other agent recognized in the field; compounded in other delivery systems, such as microspheres or liposomes; or administered in a living vector system.

The invention is described in further detail in the following non-limiting Examples.

EXAMPLES

Example I

Tyrosine phosphorylation of p145 in epithelial cells in response to HGF

Figure 1B:
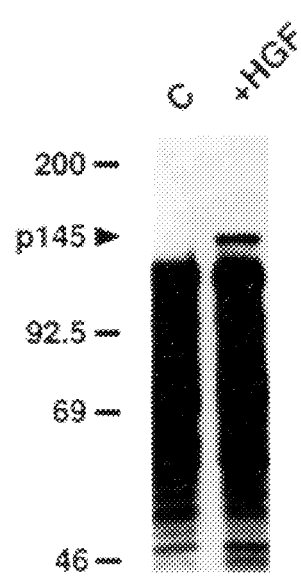
(FIG. 1B). An autoradiogram of $^{32}$P-labeled phosphoprotein from control (lane 1) and HGF-treated cells. Serum-starved cells were metabolically labeled with $^{32}$P-orthophosphate (1.0 mCi/ml) as described (White et al. in Insulin Receptors, Part A: Methods for the Study of Structure and Function, C. R. Kahn and L. Harrison, Eds. (Liss, N.Y., 1988) pp. 125–147). The cells were treated with HGF (100 ng/ml) for 10 min at 37° C. as indicated, and detergent-solubilized on ice. Phosphotyrosyl proteins were immunoprecipitated with anti-pTyr and resolved by 7.5% SDS-PAGE.
Figure 1C:
(FIG. 1C). Phosphoamino acid analysis of p145 from lane 2 of FIG. 1B was performed as described (White et al. in Insulin Receptors, Part A: Methods for the Study of Structure and Function, C. R. Kahn and L. Harrison, Eds. Liss, N.Y., 1988, pp. 125–147). The dotted circles indicate the migration of unlabeled phosphoserine (pS), phosphothreonine (pT), and phosphotyrosine (pY).

The human mammary epithelial cell line B5/589 is particularly sensitive to the mitogenic effects of HGF (Rubin et al. *Proc. Natl. Acad. Sci. USA* 88, 415 (1990)). Intact serum-starved B5/589 cells were treated with HGF (approximately 100 ng/ml) for 10 min at 37° C. and solubilized on ice. Phosphotyrosyl proteins were isolated from cell lysates by immunoprecipitation with antibody to phosphotyrosine (anti-pTyr). These proteins were resolved by SDS polyacrylamide gel electrophoresis (SDS-PAGE) and immunoblotted with the same antibody. Several phosphotyrosyl proteins detected in untreated cells by this method (FIG. 1A). Treatment of intact cells with HGF induced phosphorylation of a 145-kD protein (p145) (FIG. 1A, Lane 3). B5/589 cells exposed to epidermal growth factor (EFG) displayed tyrosine phosphorylation of the EGF receptor, but not p145 FIG. 1A, Lane 3. When lysates from control and HGF-treated cells that had been labeled with $^{32}$P-orthophosphate were used for immunoprecipitation with anti-pTyr, phosphorylation of p145 was specifically detected in HGF-treated cells (FIG. 1B). Phosphoamino acid analysis of $^{32}$P-labeled p145 confirmed the presence of phosphotyrosine, and revealed the presence of phosphoserine as well (FIG. 1C). The HGF-stimulated phosphorylation of p145 on tyrosine and its apparent molecular weight were consistent with the possibility that p145 represented the receptor tyrosine kinase for HGF.

Example II

Identification of p145 as the β subunit of the c-met proto-oncogene product

A number of receptor-like molecules have been described for which there are as yet no known ligands. One of these is the c-met proto-oncogene product, which is a receptor-like tyrosine kinase comprised of disulfide-linked subunits of 50-kD (α) and 145-kD (β) (Tempest et al. *Br. J. Cancer* 58, 3 (1988), Giordano et al. *Oncogene* 4, 1383 (1989)). In the fully processed c-met product, the α subunit is extracellular, and the β subunit has extracellular, transmembrane, and tyrosine kinase domains as well as sites of tyrosine phosphorylation (Giordano et al. *Oncogene* 4, 1383 (1989); Gonzatti-Haces et al. *Proc. Natl. Acad. Sci. USA* 85, 21 (1988)).

To test the hypothesis that p145 might represent the c-met protein β subunit, proteins immunoprecipitated by anti-pTyr from control and HGF-treated B5/589 cells were immunoblotted with a monoclonal antibody directed against the cytoplasmic domain of the c-met product. Specifically, a mouse monoclonal IgG raised against recombinant human c-met protein cytoplasmic domain was used. Recognition of human c-met protein by immunoprecipitation or immunoblotting can be specifically blocked by incubating in the presence of the recombinant protein fragment.

Figure 2A:
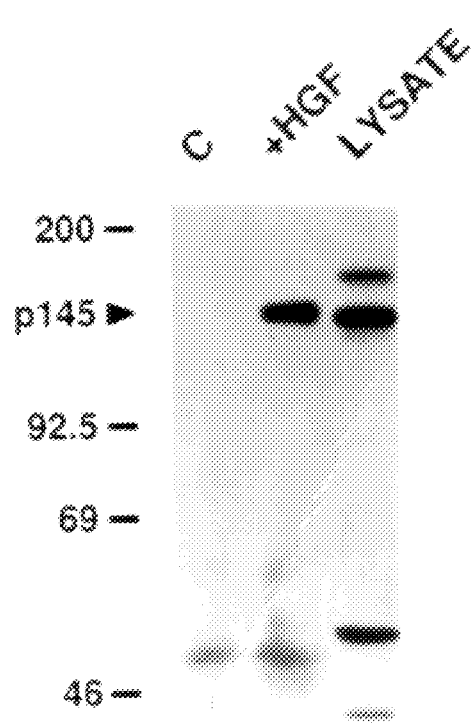
(FIG. 2A). Anti c-met immunoblot of anti-pTyr immunoprecipitates from control (lane 1) and HGF-treated B5/589 cells. Samples for immunoprecipitation (2 mg protein) were prepared as described (In FIG. 1A), resolved by 7.5% SDS-PAGE, transferred to Immobilon (Millipore) membranes and detected with monoclonal anti-c-met and [$^{125}$I]-protein-A. To quantify the percentage of c-met protein that was immunoprecipitable with anti-pTyr, 200 μg of B5/589 cell lysate (LYSATE) was resolved by SDS-PAGE and immunoblotted directly with monoclonal antibody to c-met.
Figure 2B:
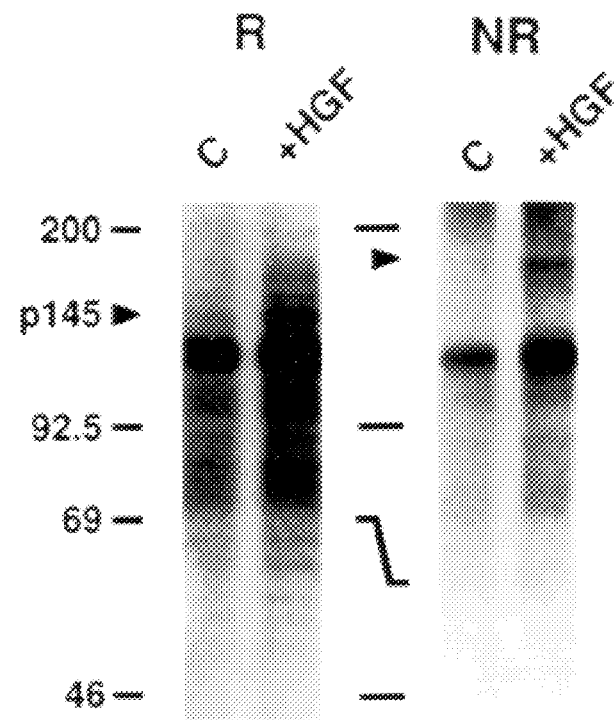
(FIG. 2B). Autoradiogram of $^{32}$P-labeled phosphoprotein from control (lanes 1 and 3) and HGF-treated B5/589 cells resolved by 7.5% SDS-PAGE under reduced (R) and non-reduced (NR) conditions. Serum-starved cells were metabolically labeled with $^{32}$P-orthophosphate, left untreated (control) or treated with HGF, and immunoprecipitated with anti-pTyr as described in, (In FIG. 1B). Samples were reduced with 100 mM β-mercaptoethanol before electrophoresis as indicted.

The prominent 145-kD protein observed specifically in HGF-treated cells FIG. 2A provided direct evidence that this mitogen induced phosphorylation of the c-met protein on tyrosine residues. When whole lysates prepared from identically treated cells were blotted directly with the c-met antibody, the percentage of c-met protein phosphorylated on tyrosine in response to HGF could be quantitated (FIG. 2A). It is estimated that at least 10% of the total cellular c-met protein content was immunoprecipitated by anti-pTyr after HGF stimulation. Analysis of the time course of HGF action revealed that the c-met protein could be recovered by immunoprecipitation with anti-pTyr within 1 min of treatment and that this effect persisted for at least 3 hours. Comparison of the electrophoretic mobility of p145 under reduced and non-reduced conditions confirmed that it was the β subunit of the c-met protein (FIG. 2B) (b)).

Without reduction, the 50-kD α subunit of the c-met protein remains disulfide-linked to the β subunit and substantially retards its migration in SDS-PAGE (Tempest et al. *Br. J. Cancer* 58, 3 (1988); Giordano et al. *Oncogene* 4, 1383 (1989); Tempest et al. *FEBS Lett.* 209, 357 (1986); Park et al. *Proc. Natl. Acad. Sci. USA* 84, 6379 (1987); Gonzatti-Haces et al. *Proc. Natl. Acad. Sci. USA* 85, 21 (1988)).

Similarly, p145 immunoprecipitated from $^{32}$P-labeled B5/589 cells that had been treated with HGF displayed a shift in mobility characteristic of the c-met proto-oncogene product when subjected to reduced or non-reduced electrophoretic conditions (FIG. 2B) (b)). Together these results identified p145 as the c-met protein β subunit and established that HGF stimulated its phosphorylation on tyrosine residues.

Example III

$^{125}$I-HGFp28 is physically associated with the c-met protein-tyrosine kinase The rapidity and extent of c-met protein tyrosine phosphorylation in response to HGF supported the possibility that c-met protein was the cell-surface receptor for HGF. However, there is evidence that receptor kinases can phosphorylate other receptors (Stern et al. *EMBO J.* 7, 995 (1988); King et al. *EMBO J.* 7, 1647 (1988)). Thus, conclusive identification of the c-met product as the HGF receptor required a demonstration of their direct interaction. $^{125}$I-labeled HGF was unsuitable for covalent affinity cross-linking because it consisted of a mixture of single chain and heterodimeric labeled species. A smaller form of HGF with similar binding properties, designated HGFp28, was $^{125}$I-labeled as a single entity and used to characterize the HGF receptor.

HGFp28 was labeled with [$^{125}$I]Na by the chloramine-T method as follows: HGFp28 (3 μg in 50 μl of 20 mM phosphate buffer containing 1.0M NaCl, pH 7.4) was reacted with chloramine-T (1.2 μg in 4 μl of phosphate buffer) and [$^{125}$ I$^{Na}$ (1 μCi) at 24° C. for 1 min. The reaction was terminated by addition of sodium metabisulfite (10 μg in 8 μl of phosphate buffer). The mixture was diluted with phosphate buffer containing 0.1% bovine serum albumin (200 μl) and applied to a column (300 μl packed volume) of heparin-Sepharose CL-6B that had been equilibrated in phosphate-buffered saline containing 0.1% BSA (PBS/BSA). The column was washed with 30 ml of PBS/BSA and eluted with PBS/BSA containing 1.0M NaCl (200 μl/fraction), removing 98% of trichloroacetic acid-precipitable radioactivity from the column. Peak fractions (specific activity: 150 to 250 μCi/μg) were 99% trichloroacetic acid-precipitable, and migrated as a single band on SDS-PAGE.

Figures 3A, 3B, 3C:
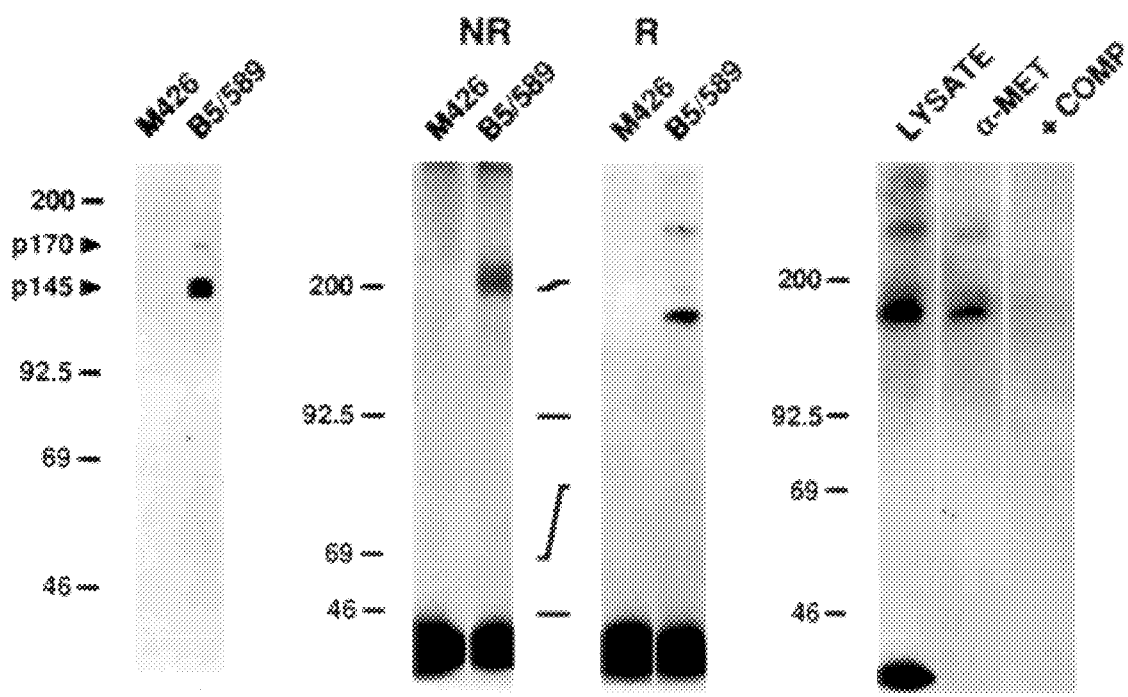
(FIG. 3A). Immunoblot of lysates (200 μg protein) prepared from M426 human lung fibroblasts and B5/589 cells using monoclonal antibody to the cytoplasmic domain of c-met protein.
(FIG. 3B). Cross-linking of $^{125}$I-labeled HGFp28 to M426 and B5/589 cells resolved by 6.5% SDS-PAGE under non-reduced (NR) and reduced (R) conditions. HGFp28 was purified as described and radiolabeled with [$^{125}$I]-Na by the chloramine-T method (Hunter et al. Nature 194, 495 (1962)). Cells were incubated with HEPES binding buffer (Bottaro et al. J. Biol. Chem. 265, 12767 (1990)) containing $^{125}$I-labeled HGFp28 (5×10$^5$ cpm) for 45 min at 25° C., washed with cold HEPES-buffered saline (pH 7.4), and treated with disuccinimidyl suberate (Bottaro et al. J. Biol. Chem. 265, 12767 (1990). The cells were then solubilized with SDS and boiled for 3 min in the presence 100 mM β-mercaptoethanol as indicated. $^{125}$I-labeled proteins were resolved by 6.5% SDS-PAGE and autoradiography at −70° C.
(FIG. 3C). Immunoprecipitation of [$^{125}$I]-HGFp28-cross-linked complexes from B5/589 cells with c-met peptide antiserum (Gonzatti-Haces et al. Proc. Natl. Acad, Sci. USA 85,21 (1988)). Sample preparation and cross-linking prior to immunoprecipitation, performed as described above, yielded the electrophoretic pattern shown in the left lane (LYSATE) under reduced conditions. The adjacent lanes show immunoprecipitation of the cross-linked species with c-met peptide antiserum (1:100) in the absence (α-MET) or presence (+COMP) of competing peptide (10 μg/ml). Immunoprecipitated proteins were absorbed to immobilized protein-G (Genex) and eluted with SDS prior to electrophoresis and autoradiography as described above.

Comparative cross-linking studies were performed using $^{125}$I-labeled HGF p28 on B5/589 cells and M426 human fibroblasts, an HGF-insensitive cell line which also lacks detectable amounts of c-met protein (FIG. 3A). The $^{125}$I-labeled HGFp28 cross-linked to its receptor on B5/589 cells migrated as a 210-kD protein in complex under non-reduced conditions (FIG. 3B). Under reduced conditions, a major 170-kD complex was observed (FIG. 3B) (b)). These apparent molecular sizes were consistent with a direct interaction between the labeled HGFp28 and the 145-kD β subunit of the c-met protein. Under reduced conditions, two minor bonds of 190-kD and about 300-kD were also detected FIG. 3B (b)). Cross-linking of $^{125}$I-labeled HGFp28 to the species observed under reduced conditions was blocked by addition of either unlabeled HGFp28 or HGF-neutralizing antisera. Under identical conditions, $^{125}$I-labeled HGFp28 failed to cross-link to any large proteins in M426 cells (FIG. 3B).

To establish that $^{125}$I-labeled HGFp28 was physically associated with the c-met protein, $^{125}$I-labeled HGFp28 cross-linked complexes were immunoprecipitated with a polyclonal antiserum (Gonzatti-Haces et al. *Proc. Natl. Acad. Sci. USA* 85, 21 (1988)) specific to the carboxyl-terminal 28 amino acids of the β subunit of the c-met protein. The covalently cross-linked major 170-kD and minor 300-kD species detected under reduced conditions were immunoprecipitated by the antibody, and their detection was specifically blocked by competing peptide ) (FIG. 3C). These results demonstrate a direct molecular interaction between $^{125}$I-labeled HGFp28 and the c-met β subunit. The composition of the minor 300-kD cross-linked species remains to be determined. All of these findings establish that the c-met product is the cell surface receptor for HGF.

Example IV

HGF stimulation of NFS-60 cells

Figure 4A:
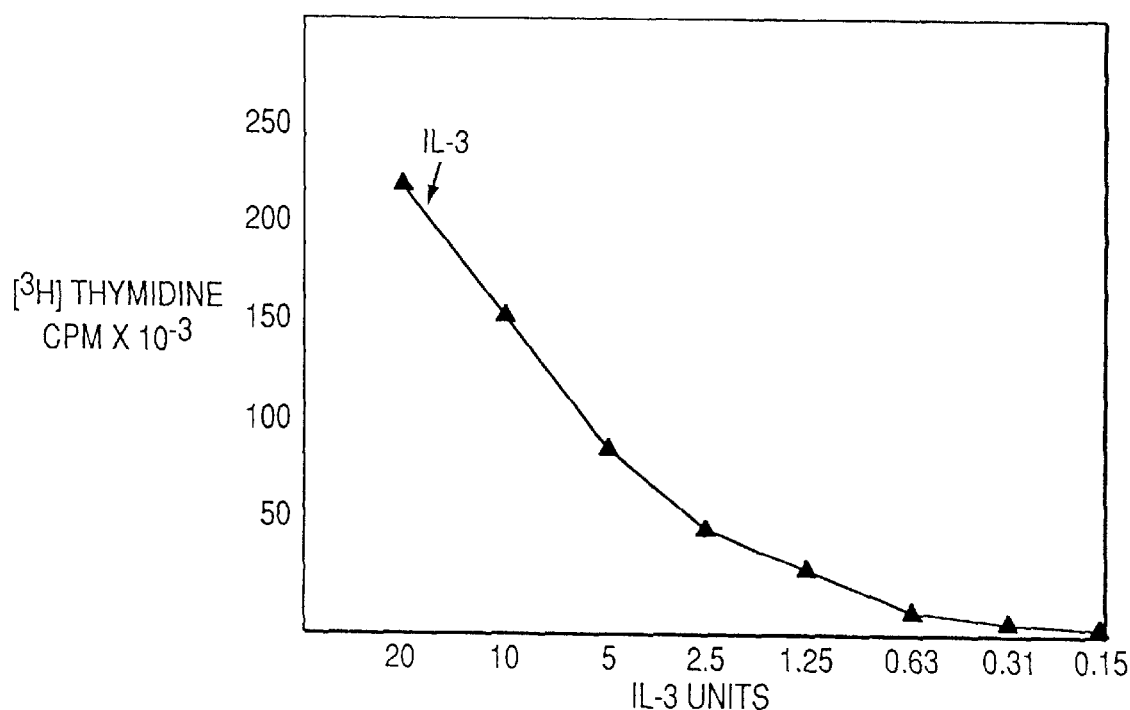
(FIG. 4A). Cells (3×10$^5$) were plated in 100 μl media. 20U IL-3 (Genzyme) was added to the first well, with decreasing amounts of IL-3 in successive wells as indicated. After 48 hours, 1 μCi [$^3$H]thymidine was added per well. The cells were incubated another 7 hours, then harvested onto filters and processed for scintillation counting. Points shown are the average of two wells.
Figure 4B:
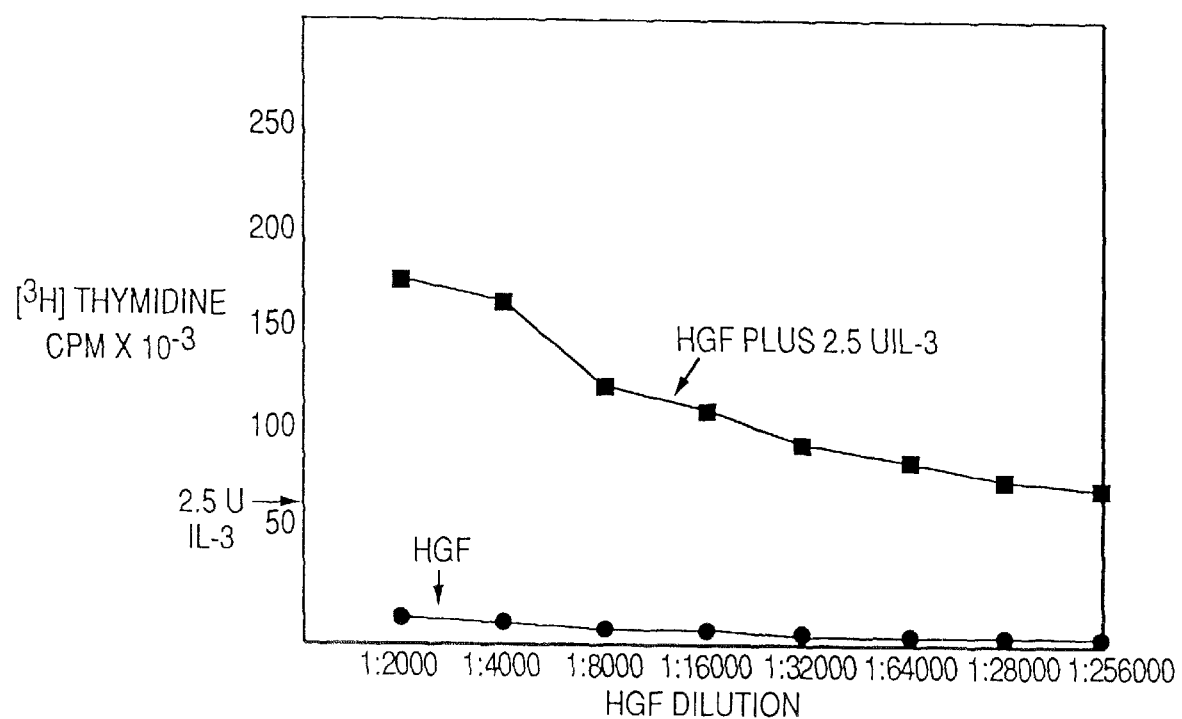
(FIG. 4B). Lower curve shows [$^3$H]thymidine uptake from addition of HGF alone. The first well received a 1:2000 dilution of HGF, with further dilutions as shown. The upper curve shows the effect of HGF when added in combination with IL-3. 2.5 U IL-3 were added per well. HGF levels were as above.

IL-3, as previously shown and repeated here for comparison, stimulated [$^{3}$H]thymidine incorporated into NFS-60 cells in a dose-dependent manner (FIG. 4A). Recombinant HGF added alone stimulated little or no incorporation of [$^3$H]thymidine (FIG. 4B). To determine whether HGF might act in synergy with IL-3, the effect of HGF on [$^3$H]thymidine incorporation was examined at predetermined suboptimal concentrations of IL-3 (2.5U) (FIG.4B). HGF added in addition to 2.5U IL-3 promoted a 3-fold increase in [$^3$H]thymidine uptake. The half-maximal level of [$^3$H]thymidine incorporation was obtained with approximately 50 ng HGF. HGF also synergized with IL-3 to promote the growth of another IL-3 dependent myeloid cell line, Da-1.

Example V

Met expression in murine bone marrow cells

Figure 5:
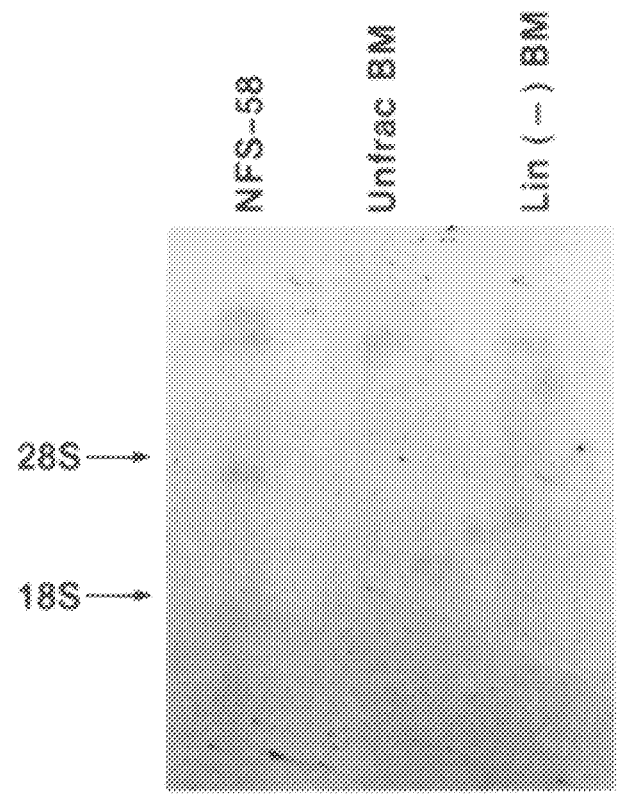
FIG. 5. Northern blot of RNA from NFS-58 myeloid leukemia line, unfractionated bone marrow, and lin- bone marrow. 10 μg total RNA was run on a 1.2% formaldehyde-agarose gel, transferred to duralose-uv, and probed with a restriction fragment containing the entire coding region of murine met. The membrane was prehybridized in (5×SSPE, 5×Denhardts, 50% formamide, 0.1% SDS, 100 μg/ml salmon sperm DNA) for 4 hours, then hybridized in the above solution containing probe labeled by random priming. The membrane was washed twice for 10 minutes each in (2×SSC, 0.1% SDS) at room temperature, then twice for 10 minutes in (0.2% SSC, 0.1% SDS) at 53° C. The membrane was exposed to X-OMAT AR film with an intensifying screen at −70° C.

Since the NFS-60 line represents a myeloid progenitor cell which is arrested in differentiation, the expression of met was examined in progenitor enriched or unfractionated murine bone marrow cells. The progenitor enriched population was prepared by removing differentiated cells from total bone marrow cells using magnetic beads and antibodies specific for antigens present on differentiated cells, giving a population of lineage negative (lin -) cells (Keller et al, *Blood* 75:596–602 (1990)). Total RNA was prepared using the RNAzol reagent, and 10 μg of each RNA was run on a formaldehyde-agarose gel. One murine myeloid progenitor line which dressed met (NFS-58) was used for comparison (FIG. Lane 1) and showed three distinct c-met mRNAs (FIG. 5). Multiple murine met mRNA species have previously been detected in several cell lines and tissues (Iyer et al. *Cell Growth and Diff.* 1, 87–95 (1990); Chan et al. *Oncogene* 2, 593–599 (1988)), and alternately spliced mRNAs have recently been described for human met (Rodrigues, et al. *Mol. Cell. Biol.* 11, 2962–2970 (1991)). Unfractionated bone marrow and lin-bone marrow both showed a single met mRNA, demonstrating for the first time met expression in bone marrow cells.

Example VI

Effect of HGF on bone marrow cells in soft agar

Figure 6:
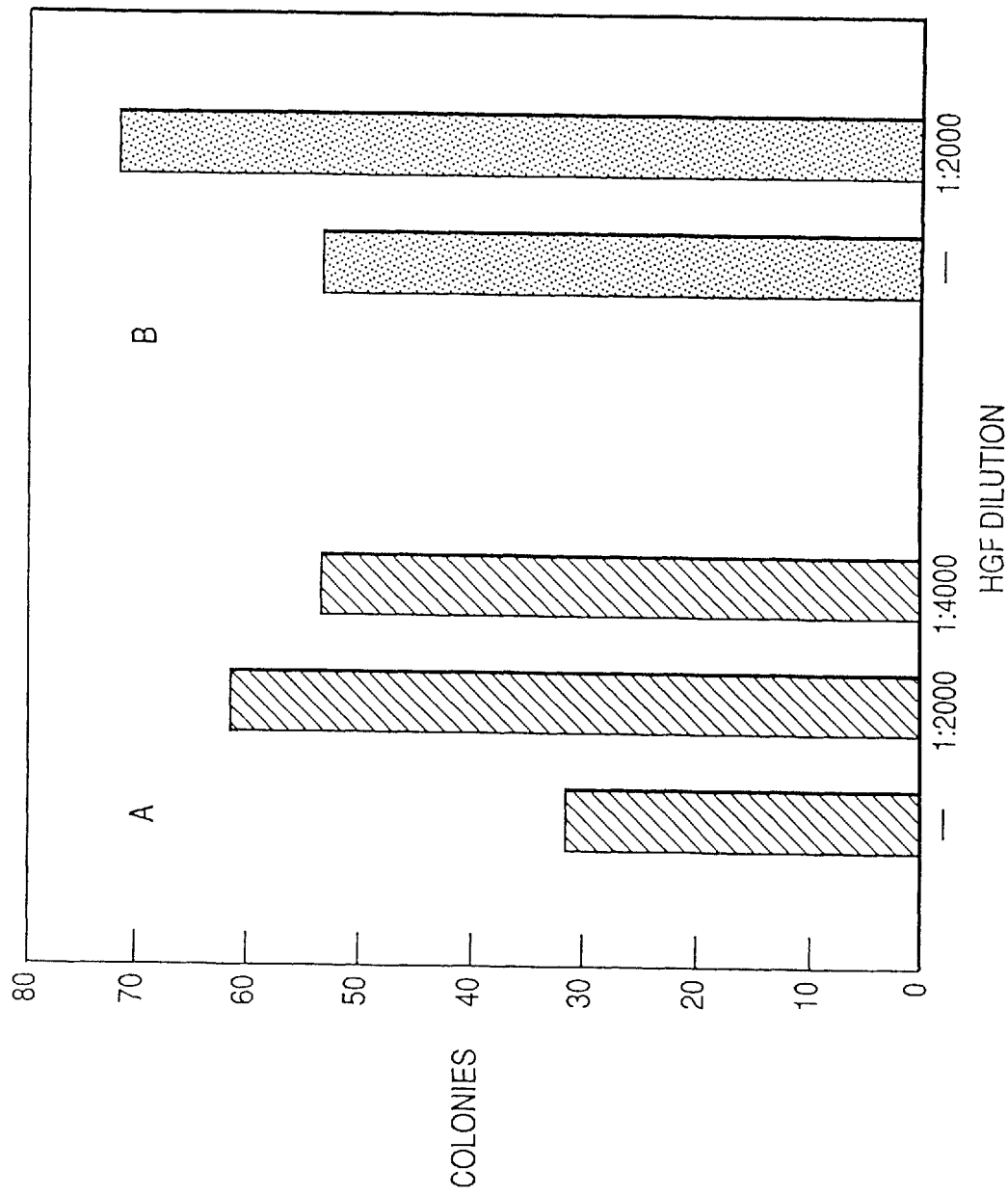
FIG. 6. Colony formation in agar of bone marrow cells.

In view of the expression of the met proto-oncogene in bone marrow cells, the effect of HGF on the growth of these cells was examined in soft agar colony assays. Similar to the results with the progenitor cell lines, HGF added to lin-cells did not result in any colony formation. However, when HGF was added to suboptimal amounts of IL-3, a 50% increase in colony formation was obtained (FIG. 6). Under similar growth conditions using suboptimal levels of GMCSF, HGF again showed a synergistic effect and enhanced colony formation by 60%. In both cases, the resultant colonies contained macrophages and granulocytes in similar proportion to that obtained with IL-3 alone, indicating that HGF did not alter the pattern of differentiation. The same pattern of stimulation was observed using murine scatter factor. Thus, the results with the lin- bone marrow cells parallel the results obtained with the NFS-60 line and indicate that HGF synergizes with CSFs to stimulate proliferation of myeloid progenitors.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A pharmaceutical composition comprising a bone marrow regeneration stimulating amount of Hepatocyte Growth Factor in combination with an amount of GM-CSF or IL-3 sufficient to enhance the bone marrow stimulating effect of said Hepatocyte Growth Factor, and a pharmaceutically acceptable carrier.

2. A method of stimulating bone marrow regeneration comprising contacting said bone marrow with a bone marrow regeneration stimulating amount of Hepatocyte Growth Factor in combination with an amount of GM-CSF or IL-3 sufficient to enhance the bone marrow stimulating effect of said Hepatocyte Growth Factor.

3. A pharmaceutical composition comprising a bone marrow regeneration stimulating amount of Hepatocyte Growth Factor in combination with an amount of GM-CSF sufficient to enhance the bone marrow stimulating effect of said Hepatocyte Growth Factor, and a pharmaceutically acceptable carrier.

4. A method of stimulating bone marrow regeneration comprising contacting said bone marrow with a bone marrow regeneration stimulating amount of Hepatocyte Growth Factor in combination with an amount of GM-CSF sufficient to enhance the bone marrow stimulating effect of said Hepatocyte Growth Factor.

5. A pharmaceutical composition comprising a bone marrow regeneration stimulating amount of Hepatocyte Growth Factor in combination with an amount of IL-3 sufficient to enhance the bone marrow stimulating effect of said Hepatocyte Growth Factor, and a pharmaceutically acceptable carrier.

6. A method of stimulating bone marrow regeneration comprising contacting said bone marrow with a bone marrow regeneration stimulating amount of Hepatocyte Growth Factor in combination with an amount of IL-3 sufficient to enhance the bone marrow stimulating effect of said Hepatocyte Growth Factor.

* * * * *